United States Patent
Berg et al.

(10) Patent No.: US 9,839,762 B2
(45) Date of Patent: Dec. 12, 2017

(54) SYSTEM AND METHOD FOR REDUCING STRESS LEVELS USING COLOR, SOUND, AND AROMA THERAPY

(71) Applicant: Harmonial Corporation, Delray Beach, FL (US)

(72) Inventors: Oyvind Berg, Delray Beach, FL (US); Elisabeth Rosse, Bordeaux (FR)

(73) Assignee: Harmonial Corporation, Delray Beach, FL (US)

( * ) Notice: Subject to any disclaimer, the term of this patent is extended or adjusted under 35 U.S.C. 154(b) by 0 days.

(21) Appl. No.: 14/947,792

(22) Filed: Nov. 20, 2015

(65) Prior Publication Data

US 2016/0144150 A1 May 26, 2016

Related U.S. Application Data

(63) Continuation-in-part of application No. 13/370,524, filed on Feb. 10, 2012, now abandoned.

(51) Int. Cl.
*A61M 21/02* (2006.01)
*A61B 5/16* (2006.01)
(Continued)

(52) U.S. Cl.
CPC .............. *A61M 21/02* (2013.01); *A61B 5/053* (2013.01); *A61B 5/165* (2013.01); *A61B 5/486* (2013.01);
(Continued)

(58) Field of Classification Search
CPC .................. A61M 21/00; A61M 21/02; A61M 2021/0005; A61M 2021/0016; A61M 2021/0022; A61M 2021/0027; A61M 2021/0033; A61M 2021/0038; A61M 2021/0044; A61M 2021/005; A61B 5/16; A61B 5/162; A61B 5/165; A61B 5/40; A61B 5/0488; A61B 5/0531; A61B 5/0533; A61B 5/1107
See application file for complete search history.

(56) References Cited

U.S. PATENT DOCUMENTS 5,304,112 A    4/1994   Mrklas et al.
5,318,503 A * 6/1994   Lord ..................... A61M 21/00
                                                            600/27

(Continued)

OTHER PUBLICATIONS

Biomedical Electronics, "Harmonial concept anti-stress range", Press Kit, (Oct. 2005).

*Primary Examiner* — Charles A Marmor, II
*Assistant Examiner* — Carrie R Dorna
(74) *Attorney, Agent, or Firm* — McHale & Slavin, P.A.

(57) ABSTRACT

The present invention is directed toward a system and method utilizing synchronized colors, sounds, and aroma therapy. The visual, auditory, and aromatic stimulation is intended to alleviate stress and/or anxiety by relaxing and stimulating the brain, thereby correcting any neurophysical imbalances. Reduction in the levels of stress and/or anxiety is achieved through the use of the auditory, visual, and aromatic sequences which are individually specific and systematic. The system and method is preferably provided in multiple sessions with each session providing both a mechanism for providing treatment as well as assessment, which is used to form the basis for future treatments.

22 Claims, 4 Drawing Sheets

(51) Int. Cl.
*A61B 5/053* (2006.01)
*A61B 5/00* (2006.01)
*A61M 21/00* (2006.01)

(52) U.S. Cl.
CPC ... *A61M 21/0094* (2013.01); *A61M 2021/005* (2013.01); *A61M 2021/0016* (2013.01); *A61M 2021/0027* (2013.01); *A61M 2021/0044* (2013.01); *A61M 2230/65* (2013.01)

(56) References Cited

U.S. PATENT DOCUMENTS

| | | |
|---|---|---|
| 5,694,939 A | 12/1997 | Cowings |
| 5,947,908 A | 9/1999 | Morris |
| 6,422,992 B1 | 7/2002 | Raffel et al. |
| 6,798,461 B2 | 9/2004 | Shapira |
| 7,785,249 B2 | 8/2010 | Schachter et al. |
| 2009/0192402 A1 | 7/2009 | Corn |
| 2010/0094156 A1 | 4/2010 | Collura |
| 2010/0240945 A1 | 9/2010 | Blkko |

\* cited by examiner

SYSTEM AND METHOD FOR REDUCING STRESS LEVELS USING COLOR, SOUND, AND AROMA THERAPY

CROSS REFERENCE

In accordance with 37 C.F.R. 1.76, a claim of priority is included in an Application Data Sheet filed concurrently herewith. Accordingly, the present invention is a Continuation in Part of U.S. Non-Provisional patent application Ser. No. 13/370,524, entitled "A System And Method For Reducing Stress Levels Through A Biofeedback Mediated System Using Color, Sound, And Aroma Therapy", and filed Feb. 10, 2012. The contents of the above referenced application are incorporated herein by reference in its entirety.

FIELD OF THE INVENTION

The present invention relates generally to a system and method that reduces stress, anxiety, and stress related disorders; and more particularly, to a non-pharmacological system and method which reduces the levels of stress and provides a mechanism for relaxation through a synchronized system and method which utilizes color, sound, and aroma therapy.

BACKGROUND OF THE INVENTION

Technological advances over the last 50 years have provided individuals with the tools to accomplish tasks more efficiently. While such advances have provided the necessary means to conduct business or personal tasks faster and easier, such innovation has resulted in a complex and fast-paced society. For example, smart phone technology has been developed to allow users the ability to be technologically connected to clients, co-workers, or employers when not physically at their work site. While such technology makes life simpler in many respects, the fact that the user is continuously "wired" or "connected" adds a certain amount of stress, as there is no down time in which the individual does not have to answer to the demands of clients, co-workers, or bosses.

Stress is usually defined as the "feeling" a person gets when overwhelmed or is undergoing life changing events. In fact, any type of event, either big or small, that may pose a threat to an individual's well being acts as a stressor and results in a stress response. Stress response is the body's mechanism for handling some type of trigger event, thereby allowing the body to respond. The stress response allows the individual to accomplish tasks efficiently and provides the individual the ability to react in dangerous situations in which the reaction must be automatic and swift. Accordingly, when a stress event occurs, there are definite physiological reactions that take place in the body. For example, stress situations often produce flight or fight stress reaction chemicals, such as cortisol, adrenaline, and noradrenalin. The production of these chemicals results in changes in blood pressure and heart rate, changes in breathing, and changes in muscular functioning. While changes in these systems are beneficial in the short term, long term stresses can result in pathological conditions that are harmful. Additionally, the inability to handle even short term stress can result in damage to one's physical and mental health.

Since individuals have different coping skills, treating stress has been accomplished in a variety of manners. In severe stress related diseases, and for individuals who can not find other relief means, pharmacological agents are used. These medications, however, are not always effective and can result in developing a drug dependency. Accordingly, a non-pharmacological method for reducing stress is needed.

SUMMARY OF THE INVENTION

A system and method utilizing a synchronized color, sound, and aroma therapy is described. The present system and methods synchronize frequencies of color, light, aroma, and sound to provide a sensory experience. This guided visual, auditory, and aromatic stimulation is intended to alleviate stress and/or anxiety by relaxing and stimulating the brain, thereby correcting any neurophysical imbalances. Reduction in the levels of stress and/or anxiety is achieved through use of the auditory, visual, and aromatic sequences which are individually specific and systematic. The system and method are preferably provided in multiple sessions with each session providing both a mechanism for providing treatment, as well as user assessment which forms the basis for future treatments.

The system and method combines colors, shapes, sounds, images and aroma, to de-stress the mind and body. This unique concept enables the conscious and the unconscious intelligence of the brain to react differently to stressors, thus providing a state of balance and equilibrium. Such actions are partially based on the principles of chromotherapy, music therapy, and aromatherapy.

Chromotherapy is the science that uses color to preserve and restore the body's vibrational frequencies that correspond to physical and mental wellness. It is a natural method based on the fundamental properties of each color having strength, action and temperature that characterizes and initiates reactions inside the body. Restorative effects can be obtained by using the color corresponding to the element lacking in the body or the color with the exceeding essence in the body. When balanced, optimal health is maintained or regained.

Music therapy uses the psychological, affective and relational effects of music: noises, voices, sounds, silence, breath and movement. Sound is a mechanical compression wave that propagates through a solid, liquid, or gaseous environment characterized by vibration, amplitude and tone. Music has the ability to manipulate and make us feel various and strong emotions.

The system and method in accordance with the present invention uses not only color and music, but also moving shapes and images as well as aromas to enhance the therapeutic value of the experience. Aromatherapy is also filled with vibrations of an electromagnetic spectrum. Such therapy helps promote the healing of the body as well as activating the brain's emotional centers for peacefulness of the mind. Such a system and method is adapted to create the perfect blend of color, music and aroma for an optimal session for each client.

To obtain balance, wellness and daily efficiency, the present invention creates a unique diagnostic system to create each personalized session, using one or more multiple steps, including a personalized questionnaire and sessions of senses harmonized. In the first part of the session, the user completes a questionnaire to provide a specific color based treatment. The user is then taken into the heart of their prevailing element and exposed to theme-based images, such as but not limited to, water (life awakening and perennial), air (imagination and symbol of freedom); earth (symbol of wisdom and broad-mindedness); fire (symbol of life strength, brightness and power).

During each session, the system will choose a movie based on the five theme-based elements, discussed later, using symbolic images of nature and geometry. To complete the treatment, the patient recovers their unity with meditation supported by viewing images of a mandala (geometric design symbolic of the universe) and corresponding color which enhances creativity and the ability to advance more positively toward the future. Accordingly, each session is based on four components: the association of moving shapes (concentric circles based on hypnotherapy); infusion of aromatherapy; color, sounds and music with images involving the theme-based images, and calming images such as the appearance of mandala, each corresponding with a restoring and curing color. The present invention also includes a computer based system to record all the information from one session to the next and follows the evolution of the client to adjust the parameters in order to determine and optimize results, such as the types of images viewed and the color and aroma association of the images.

An illustrative embodiment of the non-pharmacological method of reducing anxiety and stress levels within an individual in accordance with the present invention may comprise the steps of: assessing an individual's psychological status by subjecting the individual to a first treatment determining test, the first treatment determining test including administration of a questionnaire containing a plurality of pre-determined questions designed to assess the individual's emotional state; electronically analyzing data obtained from the first treatment determining test; determining a first treatment session to be administered to the user, the first treatment session based on data obtained from the questionnaire; providing a first treatment session to the individual based on data obtained from the first treatment determining test, the first treatment session comprising: exposing the user to one or more images based on a particular treatment grouping; exposing the user to auditory notes, the auditory notes having preset frequencies for the particular treatment groupings; and exposing said user to one or more aromas.

Accordingly, it is an objective of the present invention to provide a system and method for reduction of stress and/or anxiety.

It is a further objective of the present invention to provide an interactive stress management system and method designed to provide deep and lasting relaxation through stabilization and balancing of the central nervous system.

It is yet another objective of the present invention to provide an interactive stress management system and method designed to provide deep and lasting relaxation through stabilization and balancing of the central nervous system which uses a combination of color therapy, sound therapy, and aroma therapy.

It is a still further objective of the present invention to provide an interactive stress management system and method designed to provide deep and lasting relaxation through stabilization and balancing of the central nervous system which uses a combination of color therapy, sound therapy, and aroma therapy, as well as physiological analysis of the individual undergoing the treatment.

It is a further objective of the present invention to provide an interactive stress management system and method designed to provide deep and lasting relaxation through stabilization and balancing of the central nervous system which uses a combination of synchronized color therapy, sound therapy, and aroma therapy, as well as psychological analysis of the individual undergoing the treatment.

It is a still further objective of the present invention to provide a system and method which synchronizes frequencies of color, light, aroma, and sound to provide a sensory experience.

It is yet another objective of the present invention to provide an interactive stress management system and method designed to provide deep and lasting relaxation through stabilization and balancing of the central nervous system which uses a combination of color therapy, sound therapy, aroma therapy, as well as physiological and psychological analysis of the individual undergoing the treatment.

It is a still further objective of the present invention to provide an interactive stress management system and method designed to analyze the status of the patient in one session in order to provide a treatment for a following session.

Other objectives and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

The present invention incorporates and improves upon the subject matter of a previous synchronized system developed by Harmonial Corporation, (Boca Raton, Fla., USA). The previous system was based on a combination of color and sound therapy. The current system combines color and sound therapy with aromatherapy to provide an enhanced synchronized mediated therapy designed to reduce stress and/or anxiety, and to treat symptoms of individuals suffering from the effects of stress and anxiety. The current system further synchronizes specific frequencies of sound with that of color, light, and aroma to provide a more effective sensory experience. The system and method further provide evaluation methods to assess the psychological status of the user prior to or as the treatment is being undertaken. The evaluation methods provide data which is electronically analyzed by a computer system having specialized software programs which are configured to establish treatment sessions, i.e. the appearance of specific shapes and images, and arrangement and synchronization of the colors, sounds and aromatherapies.

The non-pharmacological method of reducing anxiety and stress levels within an individual as described herein provides sessions for which color treatment has been guided, or personalized, based on reactions to various testing methods. The action of the method is chromatic, sonorous, and aromatic. The personalized color treatments are designed to penetrate through the eyes and regulate the biological clock of the body through action on the hypothalamus. The hypothalamus controls the nervous system and the endocrinal system, which together regulate all the biological functions of the human body. It sends information linked to light to the pineal gland, which informs other organs of it. The cells of the pineal gland, in turn, transform the nerve impulses, resulting in conversion of luminous messages into chemical molecules.

The methodology in accordance with the present invention is used as a compliment to classical medical treatments, homeopathy, or acupuncture in order to improve the general state of the user. For any person, there exists a permanent equilibrium between the body and the psyche. Both physical and psychological negative experiences can create states of ill-being. Anxiety or depression, for example, creates imbalances in a person's cerebral hemispheres which can result in repercussions in our daily behavior, such as excessive tiredness or trouble sleeping. Treatments using color are designed to rebalance individuals suffering from imbalances resulting from physical pathologies brought about by psychological troubles, anxiety, depression, and/or troubles adapting to stress.

The methodology in accordance with the present invention further includes use of sound treatments in combination with color treatments. Use of color and sound, therefore, are designed to provide enhanced rebalancing mechanisms. Sound is a vibration which penetrates the skin and bathes our body entirely. Different sound frequencies contact our cells and our molecules in different ways and help them to adjust and re-harmonize. Sickness and physical, emotional or mental problems indicate an incorrect vibratory frequency or an energy blockage between these different levels of existence. Each color and each sound possess a vibratory frequency and harmonic interval capable of re-establishing or re-training the sick body, emotions and thoughts.

Sound is similar to color, differing by a lesser vibratory frequency. In addition, sound also has harmonic properties that color does not have. Harmonics (the sharps above fundamental sound) have the capacity to stimulate the brain (epiphysis) and to produce states of modified consciousness facilitating relaxation (alpha waves). Sound recharges the cortex and drives the nervous system. Sound travels and stimulates different zones of the brain and can balance the 2 hemispheres. Moreover, sonorous vibrations impact the body through resonance with the cellular fluids in the body. Vibrations alternating high and low frequencies, as in the sessions of the present methodology, are designed to improve functions of the mechanism of the ear. Sound allows access to emotions buried in the unconscious and favors the releasing of "emotional crystals" with the spontaneous appearance of images of the past accompanied sometimes by sadness and anger not yet transformed. Additionally, sound brings about relief through its effect on the central nervous system through improving cognitive capabilities (attention, memory) and psycho-motor capabilities through which it is known to reduce the effects of stress. The effectiveness of the methodology in accordance with the present invention is made possible by the combination of several Ayurvedic and Chinese fields of knowledge, and by the association of several techniques stimulating the sensory apparatus by the bias of hearing, sight and smell. It is this vibratory synthesis uniting waves of sound, color, and smell which act on the totality of the cerebral and corporeal functioning of the patient in order to reestablish harmonious balance.

The methodology in accordance with the present invention is designed to have an effect on the brain. As a result of cerebral plasticity, the brain modifies the organization of its networks of neurons under the influence of sounds, colors and smells, which have an immediate effect on the cerebral treatment of emotion. The two hemispheres of the brain play a role. The left hemisphere is in control of rhythm and form, while the right hemisphere controls melody, harmony, and color. The cerebral structures involved are found in the right medio-temporal lobe, where they are stimulated. The hippocampus is important for the functioning of memory and the fine analysis of harmony. The amygdala region is important in regulation of emotions. The hypothalamus is essential for the regulation of biological rhythms. It has been shown that sound has an influence on cerebral activity, through the effect of resonance within the bony, muscular, tissue, or nerve structures of an individual, influencing the pulse, breathing and emotions, lowering arterial tension, cardiac rhythm, and muscular tension which reverberates on the spirits and anxiety. The impact of the methodology in accordance with the present invention contributes to re-harmonizing the electromagnetism of the brain. The visualization of colors, as well as the combined action of sounds and smells spread sonorous, chromatic and olfactory rebalancing vibrations through the skin and mucus, causing internal regulation in the vibratory behavior of the cells. In addition, the method works as a result of the symbolism of the images and forms used.

In general, the system works using several components, an evaluation, development of the treatment of a session based on the evaluation, and debriefing. The evaluation uses a plurality of testing modalities. A questionnaire is used to define the general profile of the patient. From the analysis of the questionnaire, an energy profile of the patient will be determined, allowing the establishment of personalized sessions during which one color and its complement, images relating to theme based criteria, such as fire, earth, wood, water, and metal, representing symbolically the emotional state of the patient will be used, and additional images, such as mandala (circle) and a rainbow will be utilized. One or more scents will be used in conjunction with the color/sound/image treatments.

As an illustrative example, if the results of the evaluation demonstrate an excess of humidity as determined by responses to the questionnaire, the color green, whose frequency will spur the body to produce a drying reply will be used, and the element theme based images of water representing the current state of the patient will be proposed. In fact, each color sends to the body a "code" message in the form of electromagnetic radiation of a determined length of waves, and each frequency generates a unique effect. Each element symbolically represents an interior state, which, if it is put into images, may help to change the emotional state of the patient. Such emotional state can be associated with, among others, four qualities, hot, cold, dryness and humidity. The method in accordance with the present invention, through the visualization of colors of wave form, in combination with the action of symbols, sounds and smells, spreads through the sensory apparatus, the skin and mucus, sonorous, olfactory vibrations (aromatic molecules are caught by thousands of chemo-receptors in the olfactory epithelium to be transmitted to the olfaction center, in the heart of the limbic brain, which controls our neuro-vegetative system and all our psychological states, provoking psychic effects, reactions independent of will, which may allow the modification of behaviors with regard to addictions: bulimia, nicotinism, alcoholism) leading to an internal regulation in the vibratory behavior of cells.

Figure 1:
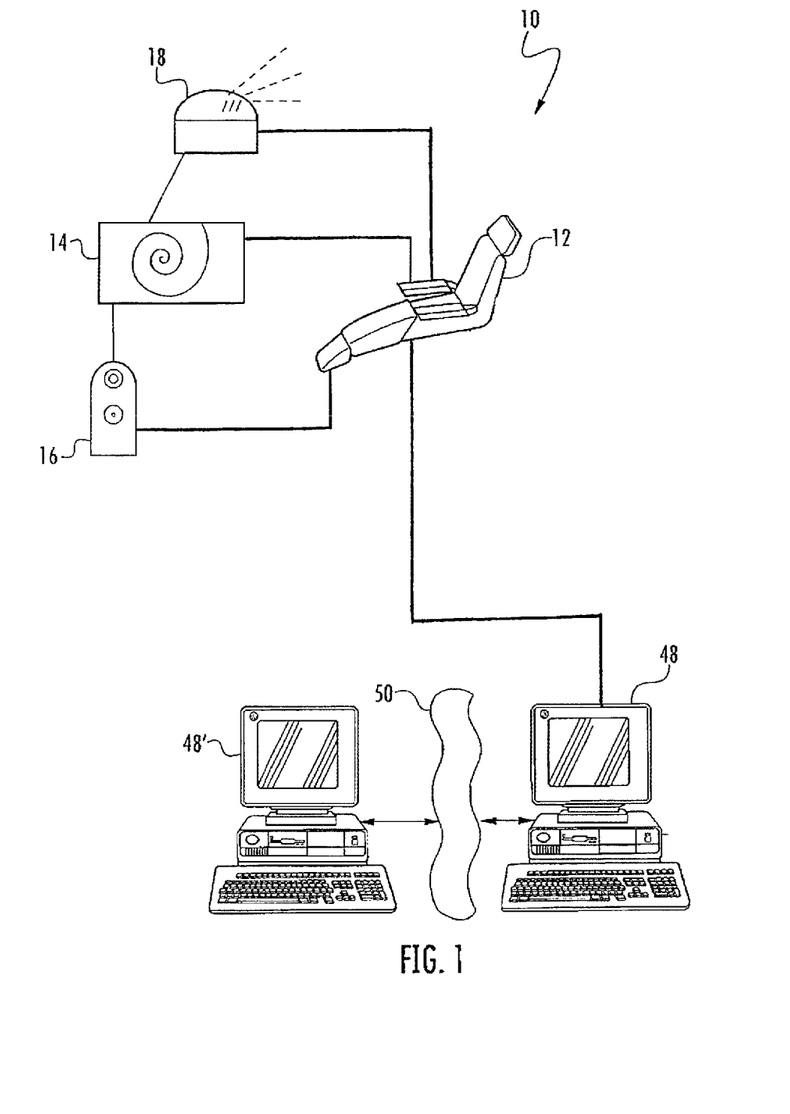
FIG. 1 is a schematic diagram of the hardware components of the stress and anxiety reducing synchronized system in accordance with one embodiment of the present invention.

Referring to FIG. 1, a schematic diagram of the hardware components of the anxiety and stress reducing sensory synchronized system 10 in accordance with an exemplary embodiment of the present invention is illustrated. The anxiety and stress reducing sensory synchronized system 10 includes a patient resting zone 12. The patient resting zone 12 may include a chair, couch, arm chair, or dental-style chair, in which the individual seeking treatment may sit and/or lay comfortably while viewing or receiving one or more visual, audible, and aromatic stimulating programs. One or more display units 14, such as a flat screen LED television, a plasma television, television monitor, or an HDTV projection unit, are placed within a viewable distance from the patient resting zone 12. One or more electromechanical devices for producing sound 16, such as a speaker, are used to provide the user with a variety of auditory experiences. An aroma dispensing device 18 is utilized to provide a mechanism that dispenses volatile plant materials, essential oils, or aromatic compounds to the user. The resting zone 12, the one or more display units 14, the electromechanical devices for producing sound 16, and the aroma dispensing device 18 can be designed as a single unit. In an alternative embodiment, one or more of the components may be placed in goggles and/or within a helmet.

Figure 2:
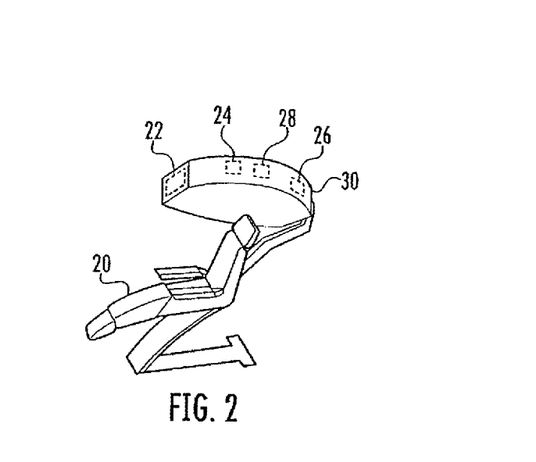
FIG. 2 illustrates an embodiment of the anxiety and stress reducing synchronized system in which the visual, audible, and aromatic components are assembled as a single unit.
Figure 3:
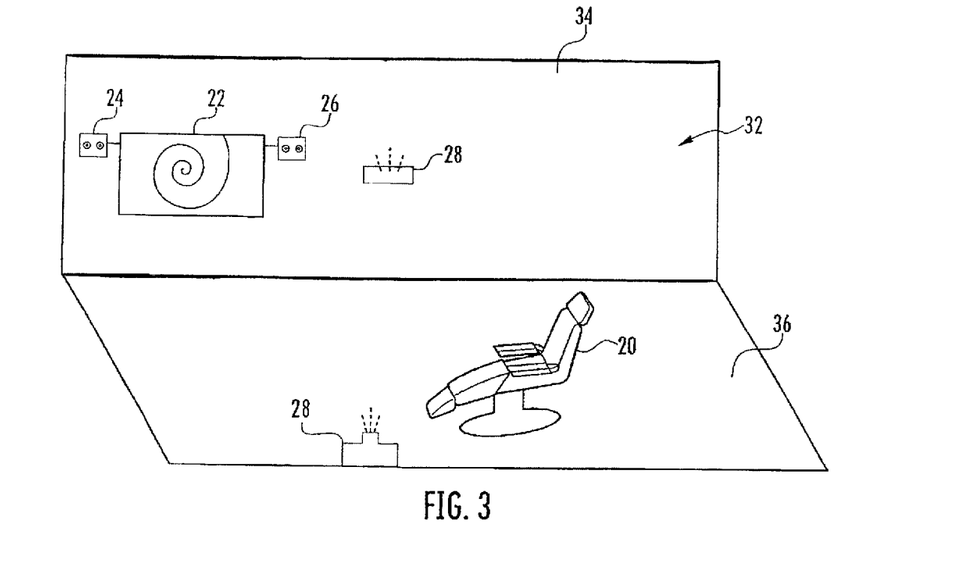
FIG. 3 illustrates an embodiment of the anxiety and stress reducing synchronized system in which the visual, audible, and aromatic components are assembled as independent components.

FIG. 2 illustrates a single unit embodiment in which the patient resting zone 12, illustrated herein as a reclineable dental-style chair 20 includes an LCD television monitor 22, a plurality of speakers 24 and 26, and an aroma dispensing unit 28 integrated into unit 30. The unit 30 is attached to the reclineable dental-style chair 20. Alternatively, the anxiety and stress reducing sensory synchronized system 10 includes the reclineable dental-style chair 20, the LCD television monitor 22, the plurality of speakers 24 and 26, and the aroma dispensing unit 28 as separate units arranged in a predefined space, such as an enclosed room 32, and placed on walls 34 and/or the floor 36 of the enclosed room 32, see FIG. 3.

A main computer 48 can be used to provide information to the user or obtain information from the user. The main computer 48 preferably contains one or more of: Central Processing Unit (CPU), memory, storage, input control, modem, network interface, and the necessary software specifically designed to provide analysis and determinations of treatment options. Additionally, one or more remotely located computer 48' can be used for storage and/or data analysis. Remote computer 48' is accessible through the internet 50. The microprocessors or computers used within the system may contain one or more algorithms stored within a memory for correlating data from the analysis portion (questionnaire) to create a treatment session, such as a video having a particular sequence of color, sound, aroma, and visual image exposure to the user. In addition, data analysis may generate corresponding frequencies of sound with the color and visual images displayed.

The anxiety and stress reducing sensory synchronized system is an interactive stress management system which is designed to provide a method which synchronizes frequencies of color, light, aroma, and sound to provide a sensory experience for deep and lasting relaxation through stabilization and balancing of the central nervous system. The method in accordance with the present invention is unique in that it is designed to provide a sensory experience which reduces stress, while providing a determination of the individual's receptivity to color, sound, and aroma in order to characterize treatment effectiveness to provide future color, sound, and aroma treatment sessions.

In use, the anxiety and stress reducing sensory synchronized system 10 provides individualized, progressive treatments using color, music, and aromatherapy which are unique to each user and based on data generated as the user undergoes one or more treatment sessions. The auditory, visual, and aromatic stimulation is designed to alleviate and correct any neurophysiologic imbalances. The method includes exposing users to videos designed to incorporate color, visually themed images and music in combination with aromatherapy.

The method of treatment in accordance with the present invention is performed in a series of progressive sessions. Each session is designed to provide a program, i.e. video session, which combines color therapy, specific music therapy, and aromatherapy to reduce the levels of stress and/or anxiety of the user. One of the main components of the treatment is the use of colors to preserve or restore the body frequency corresponding to physical and mental health. Reduction of stress and anxiety can be accomplished by using color-based therapy and/or by providing color based treatment options based on color-associated imbalances. The color treatment includes both exposure to colored light, colored images, and theme-based images associated with a particular color, see Table 1. Additionally, each color treatment is matched with specific musical notes or arrangements, see Table 2, as well as specific essential oils or aromas, see Table 3. The combination of the color treatment, music treatment, and aromatherapy was found to provide enhanced reduction in stress and/or anxiety.

TABLE 1

Association of Theme-Based Images with Color Treatment:

| Color Treatment | Theme Based Therapy |
|---|---|
| White | Metal |
| Orange | Fire |
| Indigo | Earth |
| Green | Wood |
| Yellow | Earth |
| Violet | Water |
| Red | Fire |
| Blue | Water |

TABLE 2

Music Therapy: Association of Color Treatment with Music Treatment:

| Note | Note Frequencies in Hertz | Equivalent Wavelength of Note in Nanometers | Appropriate Color |
|---|---|---|---|
| A | 440.00 | 619.69 | Orange-Yellow |
| A# | 457.75 | 595.66 | Yellow-Orange |
| Bb | 472.27 | 577.34 | Yellow |
| B | 491.32 | 554.95 | Yellow-Green |
| Cb | 506.91 | 537.89 | Green-Yellow |
| B# | 511.13 | 533.44 | Green |
| C | 527.35 | 517.03 | Green |
| C# | 548.62 | 496.9 | Green-Blue |
| Db | 588.86 | 463.03 | Blue |
| Eb | 632.05 | 431.08 | Violet-Blue |
| E | 657.54 | 414.67 | Violet |
| Fb | 678.41 | 401.91 | Ultra Violet |
| E# | 684.06 | 398.59 | Invisible Violet |
| F | 705.77 | 772.66 | Invisible Red |
| F# | 734.23 | 742.71 | Infra Red |
| Gb | 757.53 | 719.86 | Red |
| G | 788.08 | 691.96 | Red-orange |
| G# | 819.87 | 665.13 | Orange-Red |
| Ab | 845.89 | 644.67 | Orange |

While the single frequencies in hertz (Hz) are used as a preferred example, the auditory component may include musical notes used with a particular color, and may be a single frequency within a range or multiple notes within the frequency may be used in various ranges, including orange treatment sessions associated with note frequencies of about 819 to about 845 Hz, red treatment sessions associated with frequencies of about 691 to about 720 Hz, yellow treatment sessions associated with frequencies of about 440 to about 491 Hz, green treatment sessions associated with frequencies of about 491 to about 548, blue treatment sessions associated with note frequencies of about 566 to about 588 Hz, indigo treatment sessions associated with frequencies of about 612 to about 632 Hz, and purple treatment sessions associated with frequencies of about 632 to about 678 Hz.

TABLE 3

Aroma Therapy: Association of Color Treatment/Theme Based/Element Therapy

| Aroma Therapy: Essential Oils | Theme Based/Element Therapy |
|---|---|
| May Cheng: *Litsea-cubeba* Eucalyptus: *Eucalyptus citriodora* Ylang Ylang: *Cananga odorata;* Tea Tree: *Melaleuca alternifia* | Images Relating to Fire |

TABLE 3-continued

Aroma Therapy: Association of Color Treatment/Theme Based/Element Therapy

| Aroma Therapy: Essential Oils | Theme Based/Element Therapy |
|---|---|
| Geranium: *Pelargonium graveolens;* Ginger: *Zingiber officinale;* Bergamont: *Citrus aurantium* ssp *bergamia;* Rosemary: *Rosmarinus officinalis* | Images Relating to Earth |
| Patchouli: *Pogostemon cablin;* Vetiver: *Vetiveria zizanoides;* Frankincense: *Boswella carterii;* Lavender: *Lavendula angustifolia;* Atlas Cererwood: *Cedrus atlantica* | Images Relating to Water |
| Clary Sage: *Salvia sclera;* Geranium: *Pelargonium graveolens;* Tangerine: *Citrus reticula;* Peppermint: *Citrus reticula* | Images Relating to Wood |
| Fir Needle Siberian/Grand/Silver: *Albies* ssp, *sibirica, A. grandis, A. alba;* Rosemary: *Rosmarinus officinalis;* Frankincense: *Boswellia carterii;* Clary Sage: *Salva sclera* | Images Relating to Metal |

Additional aromas which may be used include, for example, Clove Bud (*Syzygium aromaticum*) or Black Pepper (*Piper nigrum*).

Figure 4:
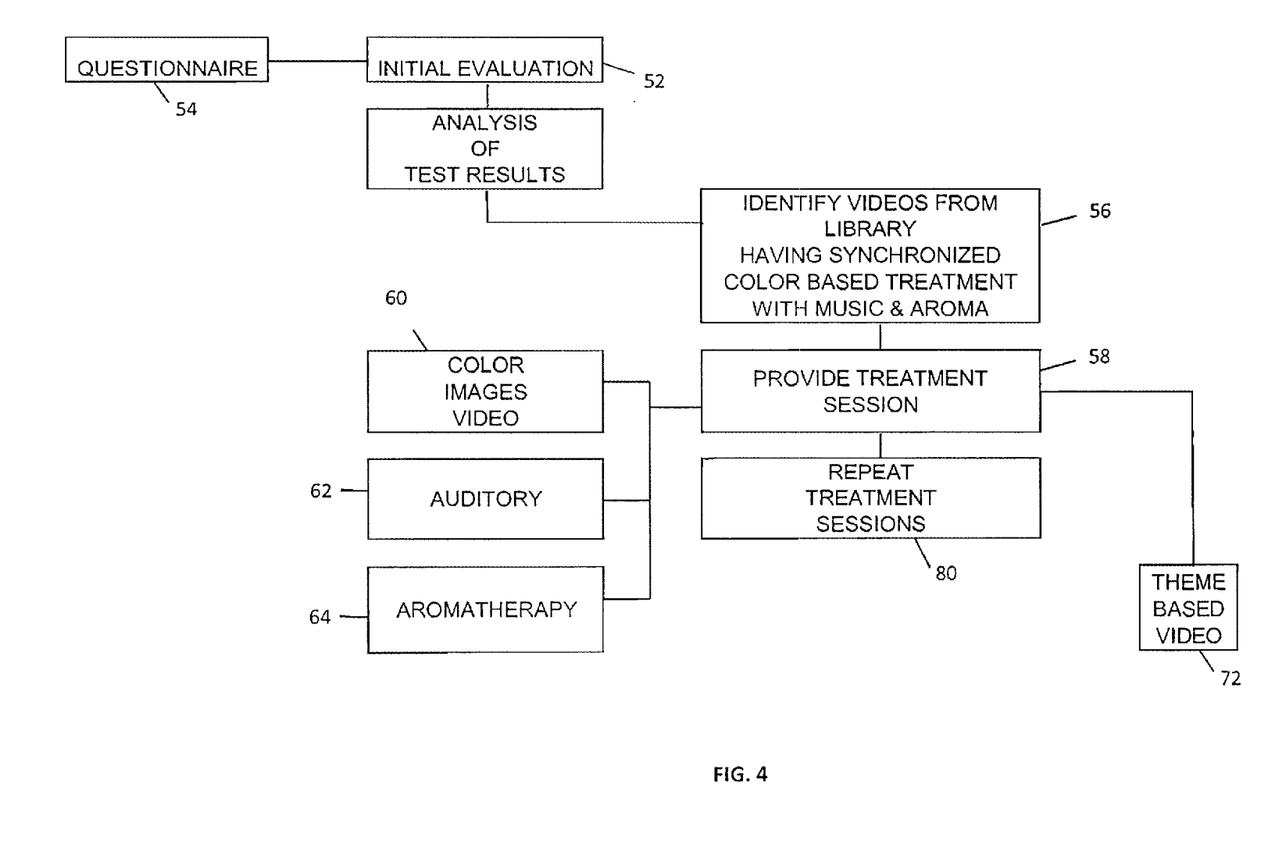
FIG. 4 is a flow chart describing an illustrative example of the steps of the method of reducing anxiety and stress in accordance with the present invention.

FIG. 4 outlines the steps undertaken for the methodology. The method consists of a plurality of analysis modules, such as a questionnaire and treatment sessions. In an illustrative example, the system utilizes one or more algorithms stored within a memory of the microprocessors or computers for correlating data from the analysis portion (questionnaire) to create a treatment session, such as a video having a particular sequence of color, sound, aroma, and visual image exposure to the user. In use, an individual desiring relaxation undergoes the first of multiple sessions. After a first initial assessment, each corresponding treatment is designed to correct any neuropathological imbalances through the synchronization of color, sound and aroma therapy. The initial session (52) includes an evaluation of the individual in order to provide the individualized, specific color/music/aromatherapy treatment. Preferably, but not necessary, the individual is placed in a quiet, secluded area and may or may not be resting on the patient resting zone 12, see FIG. 2. The individual is provided a questionnaire (54) having a plurality of questions designed to determine a treatment option based on their status, i.e. imbalance, state of stress. The questionnaire (54) is composed of psychological, spiritual and fiscal questions designed to provide direction as to the group the user will be assigned. The questionnaire may contain any number of questions specifically designed to provide an assessment of the user. For example, an illustrative embodiment of a questionnaire (54) may contain forty-two questions with each question having a two answer possibility, affirmative or negative. The questionnaire (54) is designed so that each color category has a percentage of questions which, if answered in a certain manner, leads to that color treatment being determined as the treatment color, TC. Tables 4A-4G illustrates questions associated with a forty-two question questionnaire designed to provide a color based treatment session based on user provided answers.

Table 4A illustrates six questions designed to provide color treatment of red.

| | QUESTION | RESPONSE | PREFERRED RESPONSE |
|---|---|---|---|
| 1. | Currently, do you have a cold or allergies? | Yes/No | Yes |
| 2. | Have you had an emotional or physical trauma recently? | Yes/No | Yes |
| 3. | Do you have poor circulation? | Yes/No | Yes |
| 4. | Do you have a good appetite? | Yes/No | No |
| 5. | Are you sensitive to cold temperatures? | Yes/No | Yes |
| 6. | Do you often procrastinate? | Yes/No | Yes |

The six illustrative questions are related to the TC of red, so that depending on the answers to these questions, the TC red would be chosen or eliminated. For example, if the user identified more of these questions as "YES" than any other group questions, the TC red was assigned to that person for that treatment option. After completing the questionnaire, the answers are analyzed by a software system which is programmed to determine the TC based on the answers provided.

Table 4B illustrates six questions designed to provide color treatment of orange.

| | QUESTION | RESPONSE | PREFERRED RESPONSE |
|---|---|---|---|
| 1. | Are you hyperactive? | Yes/No | Yes |
| 2. | Do you wake up several times during the night? | Yes/No | Yes |
| 3. | Do you have high blood pressure? | Yes/No | Yes |
| 4. | Are you fearful of the future? | Yes/No | No |
| 5. | Do you have a sore throat causing coughing? | Yes/No | Yes |
| 6. | Do you suffer from asthma? | Yes/No | Yes |

The six illustrative questions are related to the TC of orange, so that depending on the answers to these questions, the TC orange would be chosen or eliminated. For example, if the user identified more of these questions as "YES" than any other group questions, the TC orange was assigned to that person for that treatment option.

Table 4C illustrates six questions designed to provide color treatment of yellow.

| | QUESTION | RESPONSE | PREFERRED RESPONSE |
|---|---|---|---|
| 1. | Do you find it easy to concentrate? | Yes/No | Yes |
| 2. | Do you suffer from panic attacks? | Yes/No | Yes |
| 3. | Do you suffer from digestive problems? | Yes/No | Yes |
| 4. | Do you find it easy to deal with challenges? | Yes/No | No |
| 5. | Are you often absent minded? | Yes/No | Yes |
| 6. | Are you usually spontaneous? | Yes/No | Yes |

The six illustrative questions are related to the TC of orange, so that depending on the answers to these questions, the TC yellow would be chosen or eliminated. For example, if the user identified more of these questions as "YES" than any other group questions, the TC yellow was assigned to that person for that treatment option.

Table 4D illustrates six questions designed to provide color treatment of green.

| | QUESTION | RESPONSE | PREFERRED RESPONSE |
|---|---|---|---|
| 1. | Do you have difficulty falling asleep? | Yes/No | Yes |
| 2. | Are you often sad for no reason? | Yes/No | Yes |
| 3. | Do you have cellulite? | Yes/No | Yes |
| 4. | Are you a compulsive eater? | Yes/No | No |
| 5. | Are changes easy for you? | Yes/No | Yes |
| 6. | Do you liked to be touched? | Yes/No | Yes |

The six illustrative questions are related to the TC of green, so that depending on the answers to these questions, the TC green would be chosen or eliminated. For example, if the user identified more of these questions as "Yes" than any other group questions, the TC green was assigned to that person for that treatment option.

Table 4E illustrates six questions designed to provide color treatment of blue.

| | QUESTION | RESPONSE | PREFERRED RESPONSE |
|---|---|---|---|
| 1. | Do you have very dry skin? | Yes/No | Yes |
| 2. | Do you feel exhausted? | Yes/No | Yes |
| 3. | Are you an introverted person? | Yes/No | Yes |
| 4. | Do you have addiction? (Tobacco, alcohol, drugs, video games . . .)? | Yes/No | No |
| 5. | Do you have trouble breathing? | Yes/No | Yes |
| 6. | Do you suffer from tinnitus? | Yes/No | Yes |

The six illustrative questions are related to the TC of blue, so that depending on the answers to these questions, the TC blue would be chosen or eliminated. For example, if the user identified more of these questions as "Yes" than any other group questions, the TC blue was assigned to that person for that treatment option.

Table 4F illustrates six questions designed to provide color treatment of purple.

| | QUESTION | RESPONSE | PREFERRED RESPONSE |
|---|---|---|---|
| 1. | Do you have a backache? | Yes/No | Yes |
| 2. | Do you suffer any phobias? | Yes/No | Yes |
| 3. | Do you often lose your voice? | Yes/No | Yes |
| 4. | Do you have a good relationship with your father? | Yes/No | No |
| 5. | Do you have trouble finding your way? | Yes/No | Yes |
| 6. | Have you ever had a traumatic event or life experience? | Yes/No | Yes |

The six illustrative questions are related to the TC of purple, so that depending on the answers to these questions, the TC purple would be chosen or eliminated. For example, if the user identified more of these questions as "Yes" than any other group questions, the TC purple was assigned to that person for that treatment option.

Table 4G illustrates six questions designed to provide color treatment of indigo.

| | QUESTION | RESPONSE | PREFERRED RESPONSE |
|---|---|---|---|
| 1. | Are you creative? | Yes/No | Yes |
| 2. | Do you follow your intuition? | Yes/No | Yes |
| 3. | Do you feel you are fulfilling your abilities in life? | Yes/No | Yes |

| | QUESTION | RE-SPONSE | PREFERRED RESPONSE |
|---|---|---|---|
| 4. | Right now, do you feel bad about yourself? | Yes/No | No |
| 5. | Are you possessive with regards to people or property? | Yes/No | Yes |
| 6. | Do you currently feel stressed? | Yes/No | Yes |

The six illustrative questions are related to the TC of indigo, so that depending on the answers to these questions, the TC indigo would be chosen or eliminated. For example, if the user identified more of these questions as "Yes" than any other group questions, the TC indigo was assigned to that person for that treatment option.

Once the questionnaire has been undertaken, the results are used to provide direction as to the group the user is assigned. The computer program considers the user's highest number of preferred responses to all the questions. As an example, if the highest amount of preferred responses, in this case a "Yes" response, is taken from the red based questions, the program chooses the color red as the color of treatment. If individuals give the same amount of preferred responses in two different categories, the program may choose white for the color treatment or may choose one of the two colors randomly. If three or more colors have the same score, a determination of white as the color treatment will be made. Based on the color treatment determined, the theme based/element therapy will be used according to Table 1.

Figure 5A:
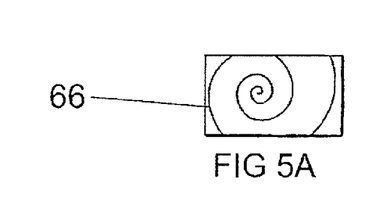
FIG. 5A is an illustrative example of images of the geometrical shapes, such as a colored spiral, associated with the treatment videos.
Figure 5B:
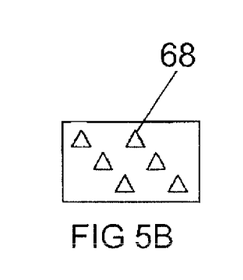
FIG. 5B is an illustrative example of images of the geometrical shapes, such as colored triangles, associated with the treatment videos.
Figure 5C:
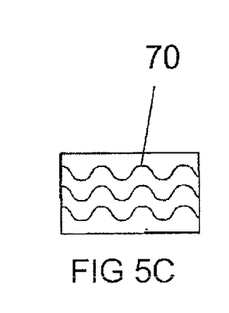
FIG. 5C is an illustrative example of images of the geometrical shapes, such as colored waves, associated with the treatment videos.
Figure 6A:
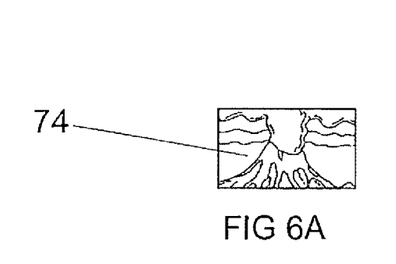
FIG. 6A is an illustrative example of a theme-based image, such as a volcano eruption, associated with the treatment videos.
Figure 6B:
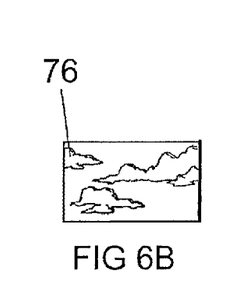
FIG. 6B is an illustrative example of a theme-based image, such as clouds in the sky, associated with the treatment videos.
Figure 6C:
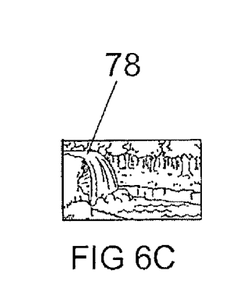
FIG. 6C is an illustrative example of a theme-based image, such as a water fall, associated with the treatment videos.

Determination of the TC through information obtained by the questionnaire (54) constitutes the first session and provides the user with an individualized treatment session. The treatment session comprises a synchronized combination of color, music, and aromatherapy designed to impact the brain and provide deep and lasting relaxation through stabilization of the central nervous system. Analysis of the questionnaire test results is used to identify videos from a video library (56) containing variations of video scenes that are correlated to the data received from the analysis steps of the method. Such videos are used as the treatment session (58) containing color images (60), auditory (62), and aroma therapy (64). Each video is specifically designed to be used based on the condition of the individual as determined by initial testing and previous treatment session. Preferably, the treatment session lasts between 10 to 26 minutes, but can be designed to be of longer or shorter duration. The treatment preferably contains three parts. The first part includes color based video images shown to the individual, preferably lasting 4 to 7 minutes. This portion of the video contains color exposure and geometrically shaped images that move upon a screen or display unit, such as moving swirls (66), moving triage (68), or moving waves (70), see FIGS. 5A-5C. The video further contains music which contains one or more specially arranged pitches, frequencies, and arrangements to coincide with the movement of the colors and/or geometrically shaped images, see, for example, Table 2. The treatment session further provides for a 5 to 10 minute video which subjects the user to images based on a particularized theme (72). The theme-based video (72) may be shown to the user as a continuation of the color bath video, or may be a separate independent video. The particular theme is arranged to provide images, colors, or combinations thereof, which accomplish body harmonization and stability. In contrast to the video which displays geometrical shapes, the theme-based video includes images of objects such as, but not limited to, water and bubbles or a gong, or particular scenery, settings, or landscapes, see, for example, volcano (74), sky with clouds (76), and waterfall/forest (78) shown on FIGS. 8A-8C. As an illustrative example, the theme-based video session may focus on providing images based on one or a combination of 1) earth, such as images of forest, trees, passageways through a mountain, sand dunes; 2) fire images that connote fire or scenes, such as images of flames, volcano eruption, fire burning scenes or fireplaces, images of the sun rising over a desert, fire at the peak of the mountain, fire from a candle, flame from a kiln, fire from the base of a mountain; 3) water, such as images of waves, ponds, streams, rivers, boiling water, water falls, rain, vast ocean, flowing water; 4) wood, such as images of weeping willows, trees on a plain, trees in a forest, or mulberry trees; 5) metal, such as images of gold, gold jewelry, stones, metal swords, gold beneath the sea, gold tip of a sword, white gold, or gold candlesticks. Table 5 provides an illustrative example of theme based videos associated with particular color based treatment sessions. The treatment session further contains a third video portion which includes providing images which result in a calming effect, preferably images that aid in meditation or trance induction. An illustrative example may include one or more images of a mandala and/or a rainbow.

During the entire session, or intermittently throughout the session, the user is not only visualizing the video, but is also being subjected to one or more aromas diffused directly to the user or within the treatment area. The one or more aromas that the user is being subjected to is specifically designed to work in combination with the particular videos, i.e. images, colors, and music, to effect the user in a particular manner. Referring to Table 3, the aroma that the user is exposed to corresponds to the particular color treatment. For example, should the TC be determined to be red, a carnation or rose fragrance will be used. Similarly, if the TC is determined to be orange, an orange flavored fragrance will be used as the aromatherapy. While Table 3 illustrates various fragrances, other fragrances may be used and the list is not intended to be limiting.

Additional treatment sessions (80) are undertaken by the individual. Each additional treatment is executed in the same manner. Accordingly, each session will contain a questionnaire (54) and analysis. The questionnaires used for additional sessions may be different than the initial questionnaire. Tables 5A-5B provide illustrative examples of session questionnaires.

Table 5A: $2^{nd}$ Session Questionnaire:
Question 1. How do you feel today?

| | YES ANSWER |
|---|---|
| Well | Indigo |
| Sick | Yellow |
| Tired | Red |
| Irritated | Orange |
| Angered | Green |
| Happy | Indigo |
| Frightened | Red |
| Sad | Green |

Question 2. What color best expresses your energy, tenacity, and happiness? The answer will determine which color gets flashed to the user.
Question 3. What time of day do you feel most energized?

| TIME OF DAY | COLOR/THEME BASED THERAPY |
|---|---|
| Morning | Green/Wood |
| Mid-morning | Red/Fire |
| Afternoon | Yellow/Earth |
| Dusk | White/Metal |
| Night | Violet/Water |

Question 4. What colors inspires you to reach your goal?
Table 5B: 3$^{rd}$ Session Questionnaire:
Question 1. How do you feel today?

|  | YES ANSWER |
|---|---|
| Well | Indigo |
| Sick | Yellow |
| Tired | Red |
| Irritated | Orange |
| Depressed | Green |

Question 2. What color irritates you and what color do you dislike the most?
Question 3. Do you have any pain or discomfort today?

| MANDALAS | COLOR THERAPY |
|---|---|
| Backache | Blue |
| Head (voices, dizziness, pressure) | Orange |
| Numbness | Yellow |
| Exhaustion | Red |
| Coping with Stress | Green |
| Falling Asleep | Blue |
| None | White |

4. Do you have problems with:

| PAIN | COLOR/THEME BASED THERAPY |
|---|---|
| Joint Pain | Orange/Fire |
| Muscle Spasms | Purple/Water |
| Throat | Blue/Metal |
| Chest | Green/Wood |
| Digestive System | Yellow/Earth |
| Genitalia | Red/Fire |
| No Pain | White/Metal |

Table 5C: 4th Session Questionnaire:
Question 1. Do you feel better since last session?

| RESPONSE | ACTION |
|---|---|
| Yes | Repeat Last Session |
| No | Repeat First Session |

Based on the responses to the questionnaire in each new session, a new TC is determined. The new TC forms the basis of the type of video session, corresponding color therapy and corresponding images, music therapy, and aromatherapy the user will be exposed to.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention, and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A non-pharmacological method of reducing anxiety and stress levels within an individual comprising:
    assessing an individual's psychological status by subjecting said individual to a first treatment determining test, said first treatment determining test including administration of a questionnaire containing a plurality of pre-determined questions designed to assess said individual's emotional state;
    electronically analyzing data obtained from said first treatment determining test;
    determining a first treatment session to be administered to said individual, said first treatment session based on data obtained from said questionnaire;
    providing a first treatment session to said individual based on data obtained from said first treatment determining test, said first treatment session comprising:
    using an electronic display unit to expose said individual to a color treatment, said color treatment including exposure to specific colored light and one or more colored images based on a particular color treatment group; and
    using a device for displaying sound to expose said individual to auditory notes, said auditory notes having preset frequencies for said particular color based treatment applied to said individual; and
    using an aroma therapy dispensing device to expose said individual to one or more aromas, said one or more aromas chosen based on said color based treatment applied to said individual;
    said electronically analyzed data obtained from said first treatment determining test resulting in said treatment session generated having a specific sequence of said colored light, said one or more colored images, said auditory notes, or said one or more aromas, wherein said electronic display unit, said device for displaying sound, or said aroma therapy dispensing device are coordinated to display or dispense said colored light, colored images, auditory sounds or aromas based on said specific sequence determined.

2. The non-pharmacological method of reducing anxiety and stress levels within an individual according to claim 1 wherein said questionnaire includes a set of questions which, when answered in a predetermined manner, assign said individual to one of said color treatment groups.

3. The non-pharmacological method of reducing anxiety and stress levels within an individual according to claim 1 wherein said color treatment groups include a red color treatment group wherein exposure to colored light and one or more colored images is based on the color red, an orange color treatment group wherein exposure to colored light and one or more colored images is based on the color orange, a yellow color treatment group wherein exposure to colored light and one or more colored images is based on the color yellow, a green color treatment group wherein exposure to colored light and one or more colored images is based on the color green, a blue color treatment group wherein exposure to colored light and one or more colored images is based on the color blue, a purple color treatment group wherein exposure to colored light and one or more colored images is based on the color purple, an indigo color treatment group wherein exposure to colored light and one or more colored images is based on the color indigo, and a white color treatment group wherein exposure to colored light and one or more colored images is based on the color white.

4. The non-pharmacological method of reducing anxiety and stress levels within an individual according to claim 3 wherein the step of exposing said individual to one or more images based on a particular color treatment grouping includes exposing said individual to a video session having a first component which subjects said individual to a video having one or more color images, and moving geometrical shapes.

5. The non-pharmacological method of reducing anxiety and stress levels within an individual according to claim 4 wherein said video session includes a second session comprising one or more theme-based images.

6. The non-pharmacological method of reducing anxiety and stress levels within an individual according to claim 5 wherein said treatment session further comprises subjecting said individual to one or more video sessions, said video sessions comprising images, shapes, theme based images, or combinations thereof.

7. The non-pharmacological method of reducing anxiety and stress levels within an individual according to claim 5 wherein said video session lasts for between 10 and 26 minutes.

8. The non-pharmacological method of reducing anxiety and stress levels within an individual according to claim 5 wherein said one or more aromas are dispensed intermittently throughout said treatment session.

9. The non-pharmacological method of reducing anxiety and stress levels within an individual according to claim 5 wherein said second session comprises images that relate to the earth.

10. The non-pharmacological method of reducing anxiety and stress levels within an individual according to claim 5 wherein said second session comprises images that relate to fire.

11. The non-pharmacological method of reducing anxiety and stress levels within an individual according to claim 5 wherein said second session comprises images that relate to water.

12. The non-pharmacological method of reducing anxiety and stress levels within an individual according to claim 5 wherein said second session comprises images that relate to wood.

13. The non-pharmacological method of reducing anxiety and stress levels within an individual according to claim 5 wherein said second session comprises images that relate to metal.

14. The non-pharmacological method of reducing anxiety and stress levels within an individual according to claim 4 wherein said auditory notes comprise one or more pitches, frequencies, or arrangements configured to coincide with movement of said color images or said geometrically shaped images displayed.

15. The non-pharmacological method of reducing anxiety and stress levels within an individual according to claim 3 wherein said blue treatment group includes said auditory notes comprising a note frequency of about 566 to about 588 Hz.

16. The non-pharmacological method of reducing anxiety and stress levels within an individual according to claim 3 wherein said red treatment group includes said auditory notes comprising a note frequency of about 691 to about 720 Hz.

17. The non-pharmacological method of reducing anxiety and stress levels within an individual according to claim 3 wherein said orange treatment group includes said auditory notes comprising a note frequency of about 819 to about 845 Hz.

18. The non-pharmacological method of reducing anxiety and stress levels within an individual according to claim 3 wherein said indigo treatment group includes said auditory notes comprising a note frequency of about 612 to about 632 Hz.

19. The non-pharmacological method of reducing anxiety and stress levels within an individual according to claim 3 wherein said yellow treatment group includes said auditory notes comprising a note frequency of about 440 to about 491 Hz.

20. The non-pharmacological method of reducing anxiety and stress levels within an individual according to claim 3 wherein said green treatment group includes said auditory notes comprising a note frequency of about 491 to about 548 Hz.

21. The non-pharmacological method of reducing anxiety and stress levels within an individual according to claim 3 wherein said purple treatment group includes said auditory notes comprising a note frequency of about 632 to about 678 Hz.

22. The non-pharmacological method of reducing anxiety and stress levels within an individual according to claim 1 further comprising providing additional treatment sessions to said individual, said additional treatment sessions comprising:

exposing said individual to specific colored light and to one or more images based on a particular treatment grouping, said colored light and said images being the same or different as said displayed in prior treatment sessions;

exposing said individual to auditory notes, said auditory notes having preset frequencies for said particular treatment groupings, said auditory notes being the same or different as said auditory notes in prior treatment sessions; and exposing said individual to one or more aromas, said one or more aromas being the same or different as said one or more aromas in prior treatment sessions.

* * * * *